United States Patent [19]
Liu et al.

[11] Patent Number: 5,492,834
[45] Date of Patent: Feb. 20, 1996

[54] METHOD OF SAMPLE PREPARATION FOR URINE PROTEIN ANALYSIS WITH CAPILLARY ELECTROPHORESIS

[75] Inventors: Cheng-Ming Liu; Hann-Ping Wang, both of Yorba Linda, Calif.

[73] Assignee: Beckman Instruments, Inc., Fullerton, Calif.

[21] Appl. No.: 91,844

[22] Filed: Jul. 9, 1993

[51] Int. Cl.⁶ .................................................. G01N 33/487
[52] U.S. Cl. .................................. 436/63; 436/86; 436/87; 436/88; 436/89; 436/161; 436/175; 436/178; 436/828; 435/4; 210/635; 210/656
[58] Field of Search ........................... 436/63, 64, 86, 436/87, 88, 89, 161, 175, 178, 813, 828; 435/23, 24, 4; 210/635, 636

[56] References Cited

U.S. PATENT DOCUMENTS 4,505,817  3/1985  Blomback et al. .................. 210/484
4,522,725  6/1985  Koyama et al. ..................... 210/639

*Primary Examiner*—David A. Redding
*Attorney, Agent, or Firm*—William H. May; Gary T. Hampson; Janis C. Henry

[57] ABSTRACT

Processes are provided for pretreating body fluid compositions and subsequently analyzing the pretreated body fluid compositions for analytes of interest. Processes for pretreating the compositions include providing size exclusion gel having a molecular weight fractionation range or a molecular weight exclusion such that the size exclusion gel is capable of excluding or fractionating the analytes of interest, and then causing the composition to contact the size exclusion gel in order to separate the analytes from low molecular weight composition components which interfere with the separation and analysis of the analytes of interest. Processes for analyzing pretreated compositions include electrophoretic methods such as capillary zone electrophoresis which involve the separation and detection of analytes of interest.

20 Claims, 8 Drawing Sheets

METHOD OF SAMPLE PREPARATION FOR URINE PROTEIN ANALYSIS WITH CAPILLARY ELECTROPHORESIS

BACKGROUND OF THE INVENTION

1. Field of the Invention

The present invention relates generally to processes for preparing body fluid samples for their subsequent analysis using sample component separation techniques. More particularly, the present invention involves methods for removing low molecular weight components from urine samples, thus providing samples which are free of compounds which interfere with the electrophoretic separation and detection of higher molecular weight species.

2. Description of Relevant Art

Proteins present in mammalian body fluids such as whole blood, serum, plasma, cerebrospinal fluids, tears, sweat, saliva and urine are useful as indicators of the presence or absence or certain disease states. Thus, the ability to identify and quantitate a variety of proteins in body fluid clinical samples can provide diagnosticians a great deal of information leading to the diagnosis of a variety of diseases.

For example, patients inflicted with kidney disease will excrete urine containing albumin and other serum proteins which are typically absent in the urine of healthy individuals. Additionally, the urine of myeloma patients is known to have free light chain gamma globulins, proteins not normally excreted in the urine of patients free of myeloma. Accordingly, techniques for identifying and quantitating these and other protein components of clinical urine samples can provide indicators of abnormal conditions such as kidney disease and the presence of myeloma in patients.

A number of techniques involving the analysis of proteins found in body fluids are known. These range from wet chemistry methods which simply indicate the presence or absence of proteins to relatively complex methods involving the separation, identification, and quantitation of proteins which may be present at very low concentrations. These methods typically involve separating the fluid components using electrophoretic or chromatographic techniques followed by detecting the separated proteins. Typically, the detection methods involve directly analyzing the separated proteins by measuring their uv absorption using a detection wavelength at which the protein has a relatively high absorbance. Other optical detection methods include those which involve labelling the sample proteins with fluorescent labels or chemiluminescent labels and then detecting the separated proteins using fluorescent or chemiluminescent detectors. All of these methods have the advantage of providing qualitative as well as quantitative information when utilized in connection with standard curves generated from known proteins of known concentration.

Since mammalian proteins are charged molecules, mixtures of proteins can be subjected to electrophoretic separation techniques resulting in the separation of the protein components. In particular, recently developed capillary electrophoresis techniques provide efficient and rapid separations of small concentrations of charged species, and have become the method of choice for the rapid separation and analysis of charged components of clinical samples.

In general, capillary gel electrophoresis involves introducing a sample into a capillary column and applying an electric field across the column. The electric field causes the charged sample components to move within the gel filled column with the direction and speed of the movement being determined by the electrophoretic mobility of each charged component. The electrophoretic mobility in turn is dependent upon the mass of each of the sample components with those components having greater mobility travelling faster than those with slower mobility. This results in the sample components being resolved into discrete zones in the capillary column.

Another form of capillary electrophoresis or "open tube" CE is similar to the above-described gel capillary electrophoresis except that the column is filled with an electrically conductive buffer solution. Upon applying an electric field to the capillary, the negatively charged capillary wall will attract a layer of positive ions from the buffer. Under the influence of the electrical potential caused by the electric field, the bulk solution must flow toward the cathode in order to maintain electroneutrality. This electroendosmotic flow provides a fixed velocity component which drives both neutral species and ionic species towards the cathode.

Typically capillary gel electrophoresis and open-tube CE utilize an on-line detector such as a uv absorbance detector or other optically based detector to monitor separations and provide quantitative and qualitative data relating to the separated components. Proteins inherently absorb in the ultraviolet spectrum at 214 nm and 280 nm, making uv detectors the detector of choice because the proteins do not require special labelling. One problem associated with using uv detection methods is the presence of low molecular weight sample components which may be present at relatively high concentrations in clinical samples. Typically, these low molecular weight components are not the analyte of interest, but absorb at the preferred monitoring wavelength, which for proteins is 214 nm. Frequently, these lower molecular weight components will co-migrate with the proteins of interest, thus causing separation and detection problems. Even when the lower molecular weight components do not co-migrate they can be present at such high relative concentrations that the lower concentration components of interest are not detected. Thus, the lower molecular weight components can substantially interfere with the detection of the higher molecular weight analytes of interest which are typically present at much lower concentrations.

Attempts to overcome problems associated with interfering sample components generally involve procedures directed toward removing the unwanted components from the sample prior to performing the separations. These procedures include subjecting the sample to dialysis to separate low molecular weight components, solvent extraction techniques to partition low molecular components, precipitation, and centrifugation. In some cases, the sample is concentrated in order to increase the concentration of analytes which are known to be present at very low concentrations and not detectable in the presence of smaller molecular weight interfering components. These procedures are tedious and labor intensive, add cost and time to the analysis process and are generally considered unacceptable by clinical practitioners.

The practice of separating low molecular weight components from clinical samples is associated primarily with procedures involving the assay of urine for Bence Jones (BJ) protein in possible myeloma patients and the analysis of certain serum proteins in proteinuria patients. The amount of Bence Jones protein in urine varies from patient to patient and can be difficult to detect in the presence of low molecular weight interfering sample components. Membrane dialysis has been effective in removing the interfering components. However, this method is cumbersome, slow and requires large volumes of buffer solutions.

Accordingly, it would be desirable to provide methods for pretreating body fluid clinical samples in order to remove clinical sample components which interfere with the analysis of the clinical samples. Furthermore, it would be desirable to provide methods for analyzing body fluid samples for certain analytes while eliminating the effects of the presence of interfering components. More particularly, there is a need to provide methods for analyzing patient urine samples for low concentrations of Bence Jones protein and other proteins indicative of certain disease states.

SUMMARY OF THE INVENTION

The present invention satisfies the above needs by providing efficient high yield processes for removing low molecular weight components of clinical samples prior to analyzing the clinical samples for higher molecular weight analytes. Because the processes of the present invention effectively remove sample components which interfere with the analysis of analyte components which can be present at much lower concentrations, the practice of the present invention allows the direct analysis of small amounts of analyte components and can preclude the need to perform sample concentration steps.

In one aspect the present invention provides processes for pretreating clinical liquid compositions prior to analyzing the clinical liquid compositions for at least one analyte having a molecular weight range. More particularly, processes of the present invention generally involve providing size exclusion gel having a molecular weight fractionation range or a molecular weight exclusion suitable for fractionating or excluding the analyte or analytes, and then causing the liquid clinical composition to contact the size exclusion gel in order to separate the analyte from any low molecular weight components of the liquid composition.

In preferred embodiments, the processes of the present invention are associated with the analysis of clinical urine samples for proteins having a molecular weight range greater than about 6,000, and involve the use of polyacrylamide or polysaccharide size exclusion gels. The size exclusion gel preferably has a molecular weight exclusion greater than about 6,000. Typically the size exclusion gel is packed in a column and a urine sample is passed through the column, providing a column eluent containing higher molecular weight proteins which have been excluded by the size exclusion gel or fractionated to the extent that they are included in the column eluent. For the analysis of urine clinical sample, higher molecular weight proteins preferably include albumin and Bence Jones proteins which are indicative of certain disease states such as kidney disease and myeloma, respectfully. Advantageously, the column eluent can be separated using methods known in the art for separating clinical sample components, and in particular, clinical urine samples.

Accordingly, the present invention additionally includes processes for pretreating clinical samples, separating the pretreated clinical sample components and determining at least one clinical sample analyte having a analyte molecular weight range. These processes typically include providing size exclusion gel having a molecular weight fractionation range or a molecular weight exclusion (or molecular weight cut-off) suitable for fractionating or excluding the analyte or analytes, and causing the clinical sample to contact the size exclusion gel, thus providing a column eluent which includes analytes which have been fractionated and eluted or excluded and eluted as determined by the analyte molecular weight. Then by subjecting the column eluent to an electrophoretic separation method and detecting analytes, the presence of any clinical sample component having a molecular weight greater than the molecular weight cut-off can be determined.

Preferred embodiments of the present invention involve the use of capillary electrophoresis (CE) separation methods and in particular open tube CE methods.

These and other advantages associated with the present invention and a more detailed explanation of preferred embodiments are described below and should be taken in combination with the following drawings.

DETAILED DESCRIPTION OF THE INVENTION

Figure 1A:
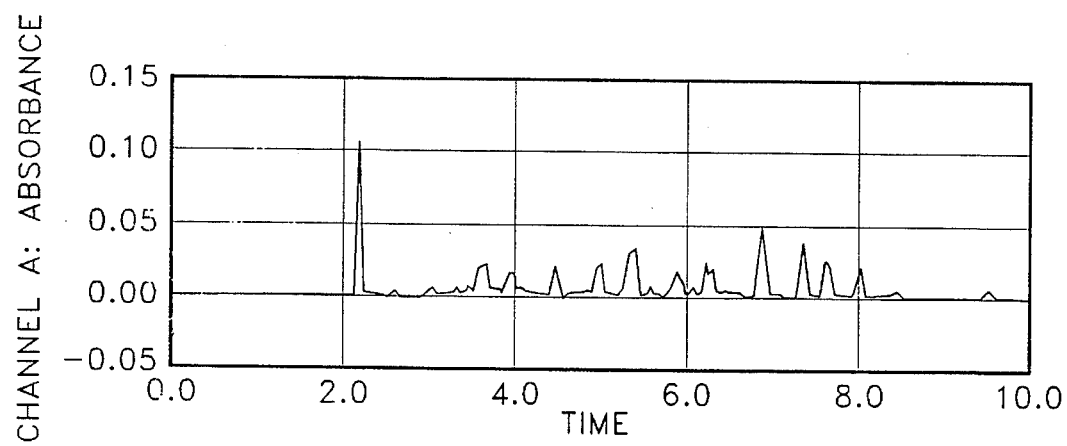
FIG. 1a is an electropherogram of a normal human urine sample which was not pretreated with size exclusion gel.

In general, the present invention involves the treatment and analysis of clinical fluid samples for certain component analytes which are of interest to clinicians and diagnosticians. More particularly, the present invention deals with treating clinical fluid samples with size exclusion gel in order to separate lower molecular weight sample components from higher molecular weight sample components prior to analyzing the fluid sample.

Typically, the methods described herein involve the efficient and quick removal of interfering low molecular weight components from clinical samples. Because low molecular weight components found in urine can interfere in the electrophoretic separation and analysis of higher molecular weight urine proteins, the present invention is particularly applicable to the analysis of urine for clinically significant higher molecular weight components. For example, Bence Jones protein and albumin each has a molecular weight greater than 10,000 and when found in urine are associated with the disease states of myeloma and kidney malfunction, respectively. However, those skilled in the art will appreciate that the present invention also finds application in any processes in which it is advantageous to separate low molecular weight body fluid constituents from higher molecular weight body fluid constituents. These include but are not limited to serum, plasma, tears, sweat, saliva and cerebral spinal fluid.

A general embodiment of the present invention includes processes for treating a clinical liquid composition prior to analyzing the clinical liquid composition for at least one analyte having a molecular weight range. The process includes the steps of first providing size exclusion gel having a molecular weight fractionation range or a molecular weight exclusion (also termed molecular weight cut-off) suitable for fractionating or excluding the analyte or analytes. Then causing the liquid clinical composition to contact the size exclusion gel results in the separation of the analyte or analytes from any low molecular weight components of the liquid composition. In performing these steps, a gel eluent is obtained which includes the analyte or analytes of interest.

As previously mentioned, the practice of the present invention preferably involves the analysis of analytes such as Bence Jones proteins found in the urine of myeloma patients as well as the analysis of serum proteins including but not limited to albumin, transferrin, $\alpha_2$ macroglobin, immunoglobulin, haptoglobin, and $\alpha_1$ antitrypsin.

Size exclusion gels suitable in the practice of the present invention include porous gel particles or beads prepared of any of a wide variety of polymeric materials. These gels are available commercially from a number of manufacturers and suppliers including BIO-RAD, Pharmacia, Pierce Chemical, and Sigma Chemicals. The particle size and particle size distribution of the gel beads is not crucial to their use in the present invention, however, appropriate sizes range from less than 20 µm to 300 µm in diameter. As will be discussed below, the diameter of the beads effects the rate at which eluent is collected as a result of contacting the liquid composition with the gel. Typically, the smaller the bead diameter, the larger the total surface area, and the slower the eluent flow rate.

When placed in contact with liquid solutions of constituents having different molecular weights, size exclusion gels having appropriate pore sizes, will exclude certain solution constituents and trap or allow other constituents to flow into the pores of the size exclusion gel beads. Typically, the totally excluded solution constituents will flow freely around the gel beads. Solution constituents or components which flow into the pores of the size exclusion gel will reside in the pores in the presence of flowing liquid for varying lengths of time. This residing time is dependent upon the molecular weight of the constituents and the pore sizes of the beads with the larger molecular weight constituents residing in the pores for less time than smaller molecular weight constituents. This phenomenon results in a molecular weight fractionation of the sample components by the size exclusion gel and the pore size of the porous gel beads determines the molecular weight fractionation properties and the molecular weight exclusion properties of the gel.

As explained in more detail below, in the context of their utility in the present invention, size exclusion gels are selected so that the gel pore size is sufficiently small to exclude body liquid components which are the analytes of interest. Similarly, the pore size is large enough to trap, without fractionating, low molecular weight sample constituents which interfere with the analysis of analytes of interest. For example, an exclusion gel having a molecular weight cut-off of about 6,000 will generally exclude molecules having a molecular weight greater than 6,000. Those skilled in the art, however, will appreciate that these molecular weights are approximate, and different types of molecules may behave slightly differently depending upon the liquid or solvent in which the molecule is dissolved and the chemical class of the molecule.

Alternatively, size exclusion gels can be selected so that they exclude analytes of interest, and/or, under the pretreatment conditions, fractionate sample components so that the analytes of interest elute from the gel and the interfering constituents remain in the gel. In this case, the gel pore size of suitable size exclusion gels is such that an analyte of interest may not be totally excluded by the gel bead pores, but flows into the pores and then out of the pores and becomes part of the eluent from the gel. In a flowing system, these are fractionated components and will elute after the totally excluded larger components. When used in accordance with the present invention these size exclusion gels trap and remove small molecular weight components which are not analytes of interest and allow larger molecular weight components which are analytes of interest to elute by totally excluding them or partially fractionating them by molecular weight. Those components which are small enough to enter the size exclusion gel pores tend to remain in the pores unless forced out by sufficient force as the result of flowing liquid.

Accordingly, in the practice of the present invention, when the appropriate size exclusion gel is brought into contact with a body liquid sample, smaller molecular weight sample components are trapped in the pores and the larger molecular weight components of analytical interest ultimately are recovered in an eluent. Thus, a size exclusion gel having a molecular weight cut-off of 40,000 and a fractionation range of 2,500 to 30,000 typically will exclude molecules having a molecular weight greater than 40,000. However, lower molecular weight molecules will be fractionated when placed in contact with these gels and elute under the appropriate conditions. As described in more detail below, such appropriate conditions depend upon the amount of wash utilized to provide the eluent and the ionic strength of the wash.

In preferred embodiments of the present invention, the size exclusion gels are prepared from hydrophilic polymers which are crosslinked in order to render the gel beads insoluble in aqueous based systems. Particularly useful hydrophilic size exclusion gel beads are prepared of crosslinked polyacrylamide or a crosslinked polysaccharide such as crosslinked dextran. However, size exclusion gels prepared from other polymers such as crosslinked polyvinylalcohol, hydrophilic crosslinked acrylates and methacrylates, and crosslinked polyvinylpyrrolidinone can also be used.

Preferred size exclusion gels have a molecular weight cut-off or molecular weight exclusion of at least 6,000. That is, when utilized in the practice of the present invention, proteins present in urine or other body fluid, and having a molecular weight of about 6,000 or less will become trapped or find their way into the pores of these gels once they come into contact with the pores of the gel material. Other suitable size exclusion gels have a molecular weight cut-off of 30,000 to 40,000, and a fraction range of 2,500 to 40,000, thus allowing solution constituents having molecular weights of 10,000 and greater to fractionate and become part of a gel eluent.

Commercially available gels suitable for the practice of the present invention include the Bio-Gel P-6 and P-30 line of crosslinked polyacrylamide gels available from BIO-RAD and the Sephadex G-25 line of crosslinked polysaccharide (dextran) gels available from Pharmacia. The BIO-RAD polyacrylamide gels are available in gel bead diameters of medium, fine, and extra fine with the medium being from 90–180 μm, the fine being from 45–90 μm, and extra fine being from 20–30 μm. Similarly, the Pharmacia dextran gels are available in fine with a diameter of 20–80 μm, medium with a diameter of 50–150 μm, coarse with a diameter of 100–300 μm, and superfine with a diameter of 20–50 μm.

Since the preferred size exclusion gels are fabricated of hydrophilic materials, prior to their use, preferably, the gel beads are swollen in distilled water. This step stabilizes the pore size, and helps maintain dimensional characteristics of the beads. Following the addition of water to the beads, it is additionally preferred that at least 3 volumes of a buffer such as phosphate buffer is passed over the size exclusion gel beads.

In accordance with the present invention, a preferred method of providing size exclusion gel is to load the gel beads in a column configured with an injection port at both ends of the column. The size of the column can vary with the volume of fluid being analyzed or brought into contact with the size exclusion gel. Preferred column dimensions which allow fast and efficient recovery are about 2 cm×0.8 cm. These columns have a gel bead capacity of less than 1 cm$^3$ and a typical void volume of about 0.3 mL. When used in accordance with the present invention one gel filled column can be used to pretreat about 0.3 mLs of urine or other body fluid. That is, a sufficient amount of fluid sample components having a molecular weight greater than the gel molecular weight fractionation range will be removed from the fluid sample. Those skilled in the art will recognize that the column configuration is non-limiting and any suitably sized container can be utilized to house the size exclusion gel.

In accordance with the present invention, after the column is filled with size exclusion gel beads, the urine or body fluid sample is applied directly to the center of one end of the column. This step causes the urine or body fluid sample to contact directly the size exclusion gel which is packed into the column. In preferred embodiments in which the column is fitted with an injection port or other opening positioned at the center of the end of the column, the fluid is directed to contact the beads at the center of the column. This precludes fluid sample simply running along the column walls without sufficient contact with the size exclusion gel.

Preferably, the urine or fluid sample is applied drop by drop and allowed to drain into the size exclusion gel packed column. In order to elute substantially all of the components excluded by the size exclusion gel and the higher molecular weight fractionated components, the next step includes applying sufficient washing buffer to the packed column and collecting the resulting eluent, comprising the excluded and suitably fractionated components, from the opposite end of the column.

The flow rate of all liquids passing through the column is proportional to the pressure drop through the column. Without the application of pressure in excess of atmospheric pressure, and particularly when fine gel beads are utilized, the additional washing step enhances the flow of eluent through the column. Additionally, the volume of washing buffer is selected so that, of the fractionated sample components, those having a molecular weight of over about 10,000 are also eluted. When size exclusion gels having a molecular weight fractionation range of 2,500 to 40,000 are utilized, urine sample volumes of 300 μl are effectively eluted from a column with a 110 mmol ionic strength buffer (ICS™) wash of about 400 μl. Those skilled in the art will appreciate that the ionic strength of the washing buffer will effect the fractionation properties of the size exclusion gel. Typically, the higher the buffer solution ionic strength, the faster the lower molecular weight components elution.

After the eluent is collected it can be stored for later analysis (preferably frozen) or analyzed immediately for analytes of interest, including Bence Jones protein and serum proteins associated with kidney disease. Accordingly, processes for separating and determining at least one analyte having a analyte molecular weight range greater than the exclusion molecular weight of the gel are additionally within the scope of the present invention. Such processes include pretreating a clinical sample as described above and then separating the eluent components and detecting the analyte or analytes of interest.

Any technique or procedure suitable for separating, identifying and/or quantitating proteins is suitable. These techniques include chromatographic methods, such as high pressure liquid chromatography, and electrophoretic separation methods. Because of the very small sample volumes required, efficiency, speed, and ease of operation, capillary zone electrophoresis (CZE) methods are preferred.

Capillary zone electrophoresis methods including capillary gel electrophoresis and open tube electrophoresis techniques for analyzing serum proteins and urine are known and those skilled in the art are credited with having the knowledge and ability to perform CE protein separations. When used in connection with analyzing urine samples pretreated in accordance with the present invention, CZE analysis can involve dilution of the eluent prior to injecting it into the capillary. It is noted that in preferred embodiments of the present invention, the eluent is diluted by approximately one haft with the washing buffer and for this reason, further dilution is not necessary. In rare clinical cases where the analyte or analytes of interest is present in extremely high concentrations, dilutions can result in enhanced analytical results. When the column eluent is diluted, suitable diluents are buffer compositions and include the phosphate buffer ICS™ available from Beckman Instruments, Inc.

A typical urine protein CZE method utilizes capillaries having an internal diameter of 25 µm, a separation length of 20 cm, and a total capillary length of 27 cm. The electric field strength applied across the capillary can vary substantially, however, for the general analysis of urine and serum protein analyses 10 kv for 7 minutes at 24° C is sufficient. Detecting the proteins which have migrated under the influence of the electric field is conveniently accomplished using an ultra-violet detector at 214 nm, a wavelength at which proteins universally absorb.

The following non-limiting examples illustrate the efficacy and advantages associated with treating clinical samples and analyzing the samples for certain analytes of interest in accordance with the present invention. It is understood that these examples are for illustration purposes only and that alternative embodiments such as the use of similar size exclusion gels and alternative analytical techniques are contemplated as within the scope of the present invention.

EXAMPLE 1

Urine samples from normal individuals were obtained and treated with size exclusion gel in order to demonstrate the efficacy of removing lower molecular weight urine components in accordance with the present invention.

A control untreated normal patient urine sample was subjected to CZE analysis by loading the sample into a 25 µm×27 µm 150 mM borate buffer silica capillary column. The column had an exterior coating of polyamide and a uv detector window disposed at 7 cm from a column outlet. The sample loading conditions were a 10 second pressure injection. After applying a separation voltage of 10 kv for 7 minutes, the migrated urine components were detected at a wavelength of 214 nm.

The electropherogram obtained from the CZE analysis of the normal urine sample is shown in FIG. 1a. All of the peaks are small molecular weight components found in normal patient urine.

P-30, a crosslinked polyacrylamide gel having a molecular weight fractionation range of about 2,500 to 40,000 was purchased from BIO-RAD. About 1 ml of the gel was washed with distilled water, packed into a small column having a diameter of 2 cm×0.8 cm, and then washed with ICS™ phosphate buffer. Excess buffer was drained from the top of the column and 300 µl of the same normal patient urine shown in the electropherogram of FIG. 1a was applied drop-wise to the top of the gel without disturbing the surface of the gel. After the 300 µl of urine had completely entered the gel bed, 400 µl of phosphate buffer was added to the gel packed column to elute proteins having a molecular weight larger than about 40,000 and to elute proteins having a molecular weight greater than about 10,000 which are fractionated by the gel. The eluent was collected and analyzed using CZE using the same conditions used to obtained the electropherogram of FIG. 1a.

Figure 1B:
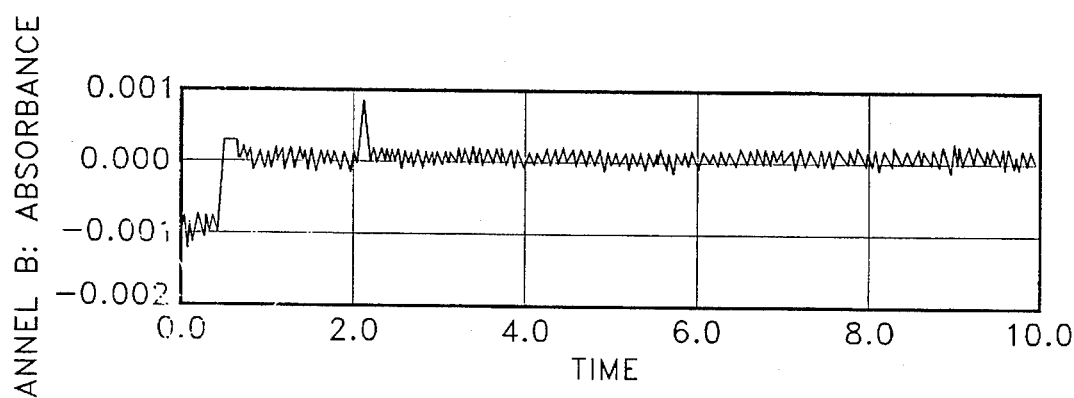
FIG. 1b is an electropherogram of the normal human urine sample shown in FIG. 1 a after contacting the sample with size exclusion gel in accordance with the present invention.

FIG. 1b is an electropherogram of the urine sample obtained from a normal patient and treated with P-30 polyacrylamide size exclusion gel as described above. The electropherogram is flat indicating the complete removal of small molecules by the polyacrylamide gel.

EXAMPLE 2

In order to show that high molecular weight proteins are excluded or fractionated and eluted by size exclusion gel, the normal patient urine subjected to the CE analysis of FIG. 1 b was spiked with an aliquot of normal human serum at a dilution of one part human serum to 9 parts of urine. The resulting combination of human serum and urine was divided into two parts. A first part was subjected to direct CE analysis using the same analytical conditions utilized to obtain the electropherograms of FIG. 1a and FIG. 1b. A second part was treated with the P-30 crosslinked polyacrylamide gel beads in the same manner as described above for the sample of FIG. 1b. This second part was also subjected to CE analysis using the same analytical conditions as the first part.

Figure 2:
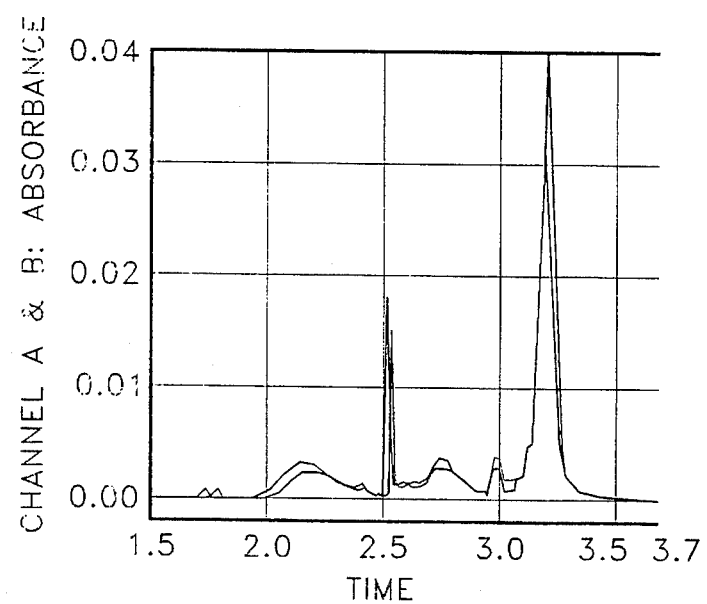
FIG. 2 illustrates electropherograms of the normal human urine sample pretreated in the same manner as that of FIG. 1b and then spiked with an aliquot of normal human serum. The sample of electropherogram a) was spiked at a ratio of one part serum to 9 parts urine and then analyzed by CE. The sample of electropherogram b) was the same as the sample of electropherogram a) except that subsequent to the spiking step, the urine sample was contacted with size exclusion gel in accordance with the present invention and then analyzed by CE.

FIG. 2 shows the electropherograms obtained from each spiked normal urine sample which was pretreated prior to spiking. The electropherogram indicated as a) was obtained from a spiked sample which was not treated subsequent to spiking the urine. The electropherogram indicated as b) was obtained from the spiked sample protreated with P-30 subsequent to spiking the urine. As illustrated by the electropherograms of FIG. 2, both samples have identical components, indicating that the pretreatment with the crosslinked polyacrylamide gel does not take-up or remove the higher molecular serum proteins which were added to the urine. Thus, size exclusion gel bead filled column allowed complete recovery of the proteins.

EXAMPLE 3

Figure 3:
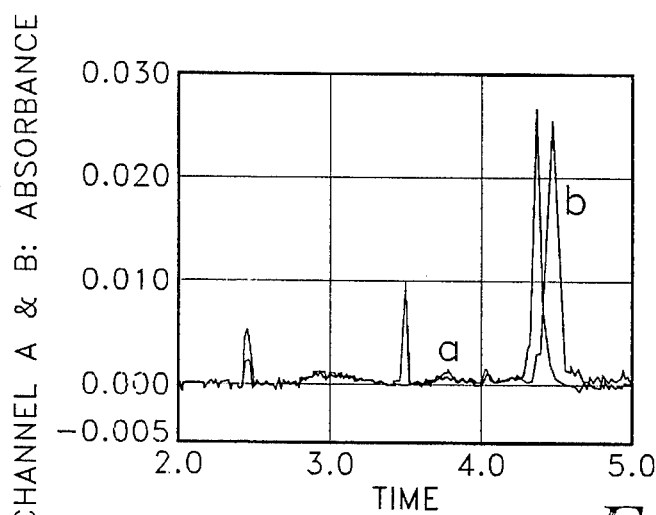
FIG. 3, electropherogram a) and b) illustrate electropherograms of samples treated in the same manner as the sample of FIG. 2 except that the sample was spiked at a ratio of 1 part serum to 79 parts urine.

In order to show that even very low concentrations of proteins are recovered using the processes of the present invention, the pre-treated normal patient urine sample prepared in EXAMPLE 1 was spiked with human serum at a dilution of 1 part serum and 79 parts urine. The spiked sample was divided into two parts, a) and b), which were treated in the same manner as described in EXAMPLE 2, respectively. A capillary electropherogram of each of the spiked urine samples is shown in FIG. 3. Electropherogram a) is that of the serum spiked normal urine sample which was not treated with the size exclusion gel after spiking. Electropherogram b) is that of the serum spiked normal urine sample which was treated with the P-30 size exclusion gel after spiking. These electropherograms indicate that even at very low serum protein concentrations, complete recovery of the proteins occurs subsequent to passing the samples through a size exclusion gel column.

EXAMPLE 4

In order to demonstrate the efficacy and accuracy of the processes of the present invention, a pathological urine sample was obtained from a patient known to have Bence Jones proteins. A portion of the sample was first analyzed for total protein and albumin on a Beckman CX-7 clinical diagnostic instrument and found to have a total protein concentration of 2.21 mg/ml and an albumin concentration of 0.0166 mg/ml.

Figure 4:
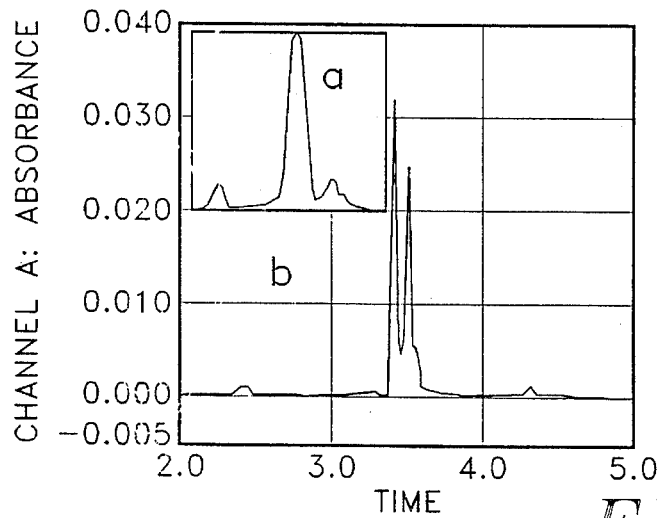
FIG. 4 illustrates electropherograms of a clinical urine sample provided by a myeloma patient. Electropherogram a) is a slab gel electropherogram of an untreated patient urine sample and electropherogram b) is a capillary electropherogram of the same sample pretreated in accordance with the teachings of the present invention.

Another portion of the pathological urine sample was treated with P-30 crosslinked polyacrylamide gel in the same manner as described in EXAMPLE 1 sample b). The treated sample was then analyzed by CZE and electropherogram b) of FIG. 4 was obtained. This electropherogram clearly shows the two Bence Jones light chain peaks. It is also evident that albumin is present at a concentration of about 1% of the total protein concentration as fully supported by the CX-7 analysis. The results of the electropherogram of the treated Bence Jones pathological sample were corroborated with a gel electrophoresis analysis of the same sample. The gel electrophoresis was performed on a Beckman Paragon SPE II instrument with the results shown in electropherogram a) of FIG. 4.

These results clearly illustrate that the processes of the present invention exclude low molecular weight components of urine samples and allow full recovery of higher molecular weight proteins which can be indicative of a pathologically abnormal condition.

EXAMPLE 5

Figure 5:
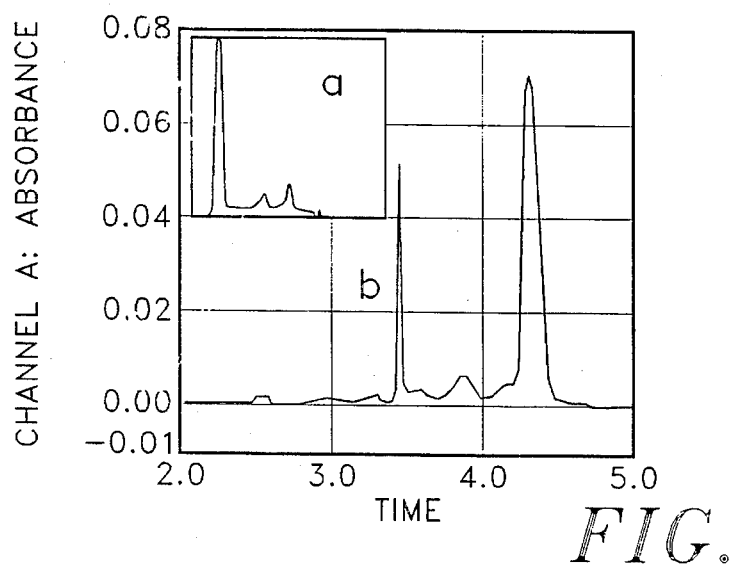
FIG. 5 illustrates electropherograms of a clinical urine sample provided by a proteinuria patient. Electropherogram a) is a slab gel electropherogram of an untreated patient urine sample and electropherogram b) is capillary electropherogram of the same sample pretreated in accordance with the teachings of the present invention.

In order to demonstrate the efficacy and accuracy of the processes of the present invention on samples containing abnormal amounts of albumin, a pathological sample was obtained from a proteinuria patient. A portion of the proteinuria pathological urine sample was treated with P-30 crosslinked polyacrylamide gel in the same manner as described in EXAMPLE 1, sample b). The treated sample was then analyzed by CZE and electropherogram b) shown in FIG. 5 was obtained. This electropherogram clearly shows the albumin which was excluded by the size exclusion gel. Additionally, low molecular weight sample components are not evident in the electropherogram, evidencing their removal by the size exclusion gel.

The results of the electropherogram of the treated abnormal pathological sample were corroborated with a gel electrophoresis analysis of the same sample. The gel electrophoresis was performed on a Beckman Paragon SPE II instrument with the results shown in electropherogram a) of FIG. 5. The albumin concentration of these samples was 5.47 mg/ml and the total protein was 7.7 mg/ml.

EXAMPLE 6

Urine samples from normal individuals were obtained and treated with size exclusion gel having a molecular weight cut-off of up to 6,000 in accordance with the present invention. These experiments were performed in order to demonstrate the efficacy of utilizing size exclusion gels having lower molecular weight cut-offs and molecular weight fractionation ranges than those used in EXAMPLES 1–5.

A control untreated normal patient urine sample was subjected to CZE analysis by loading the sample into a 25 μm×27 cm polyamide coated capillary with a detector window positioned 7 cm from a tube outlet. The sample was loaded using a 10 second pressure injection. After applying a separation voltage of 10 kv for 7 minutes, the migrated urine components were detected at a wavelength of 214 nm.

Figure 6A:
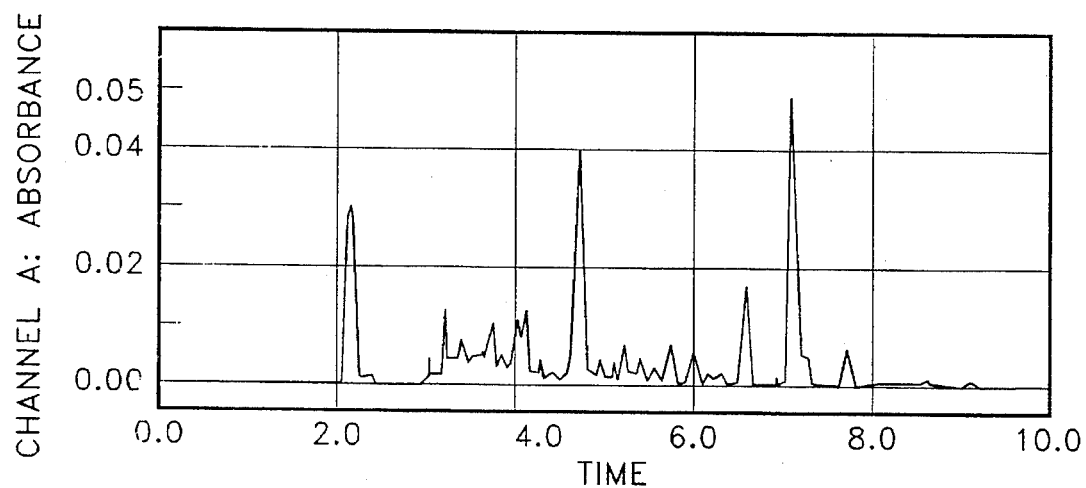
FIG. 6a is an electropherogram of an untreated normal patient urine sample.

The electropherogram obtained from the CZE analysis of the normal urine sample is shown in FIG. 6a. All of the peaks are small molecular weight components found in normal patient urine.

Figure 6B:
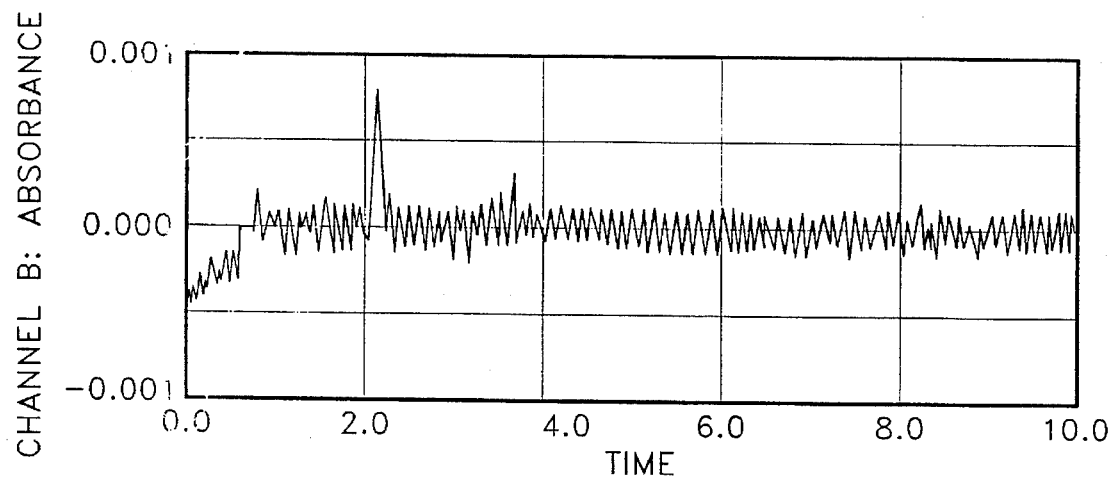
FIG. 6b is an electropherogram of a normal patient urine sample treated in accordance with the present invention.

P-6, a crosslinked polyacrylamide gel having an upper molecular weight fractionation range less than about 6,000 was purchased from BIO-RAD. About 1 mL of the gel was washed, packed into a small column, and washed with buffer as described in EXAMPLE 1. The normal patient sample was applied to the gel column, collected, and analyzed by CZE as described previously. FIG. 6b is an electropherogram of the urine sample obtained from a normal patient and treated with P-6 polyacrylamide size exclusion gel as described above. The electropherogram is flat indicating the complete removal of small molecules by the polyacrylamide gel.

EXAMPLE 7

Figure 7A:
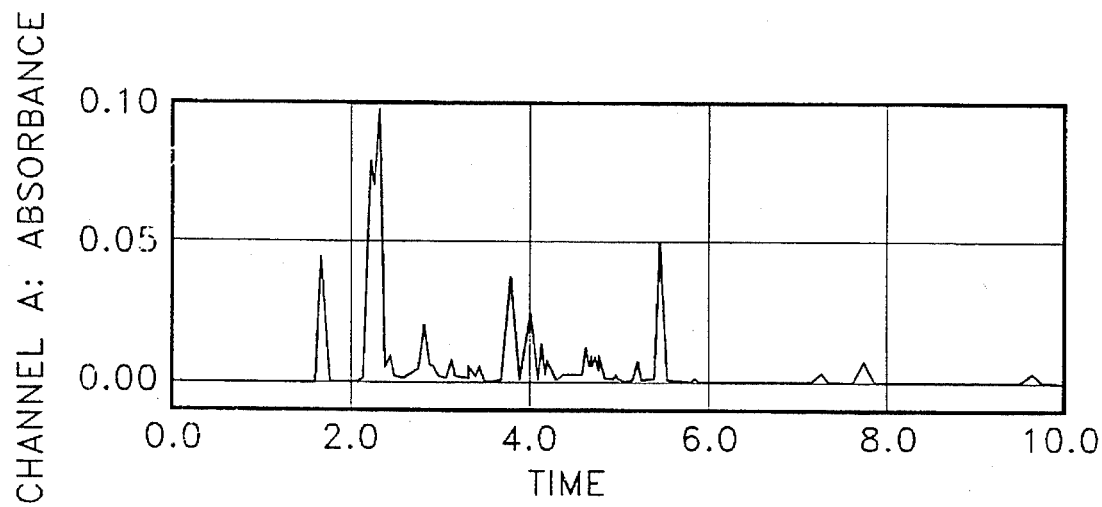
FIGS. 7a, b illustrate electropherograms of a urine sample obtained from a known myeloma patient. The sample of electropherogram a) was not pretreated and the sample of electropherogram b) was pretreated in accordance with the present invention.
Figure 7B:
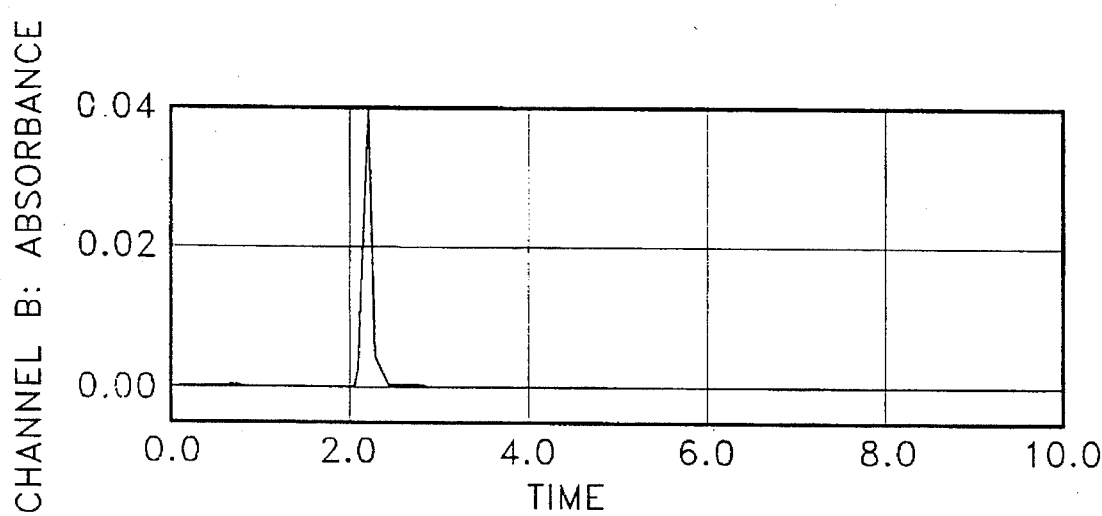

In order to demonstrate the efficacy and accuracy of the processes of the present invention utilizing a size exclusion gel having a molecular weight cut-off of about 6,000, a pathological urine sample was obtained from a patient known to have Bence Jones proteins. A first portion of the pathological sample was not pretreated with size exclusion gel and analyzed by CZE as described in EXAMPLE 6. The resulting electropherogram is shown in FIG. 7 electropherogram a) where a number of components are shown, many of which appear to co-migrate.

A second portion of the pathological urine sample was treated with P-6 crosslinked polyacrylamide gel in the same manner as described in EXAMPLE 1 sample b). The treated sample was then analyzed by CZE as previously described and electropherogram b) of FIG. 7 was obtained. This electropherogram clearly shows the Bence Jones protein.

These results clearly illustrate that the processes of the present invention exclude low molecular weight components of urine samples and allow full recovery of higher molecular weight proteins which can be indicative of a pathologically abnormal condition.

EXAMPLE 8

Figure 8A:
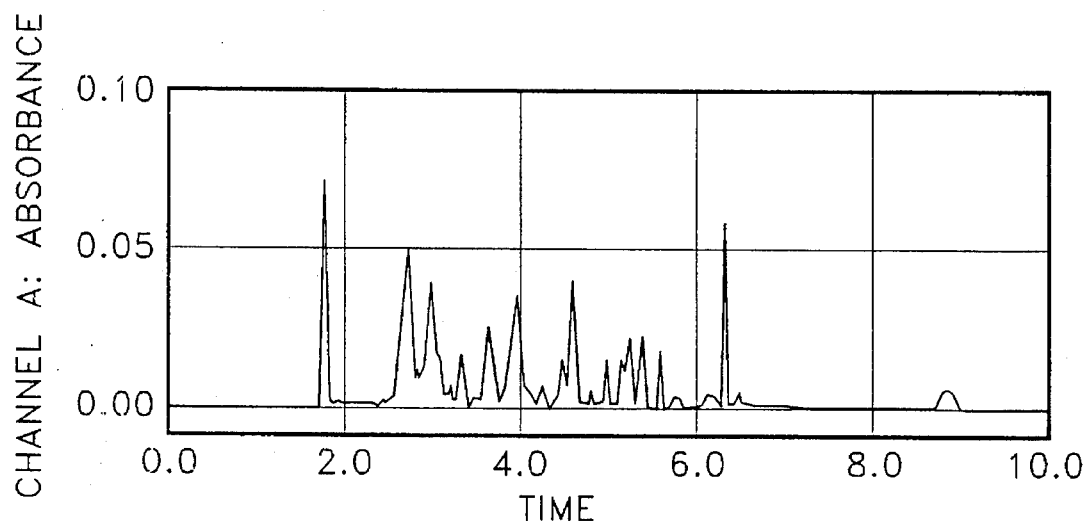
FIGS. 8a, b, illustrate electropherograms of a urine sample obtained from a known proteinuria patient. The sample of electropherogram a) was not pretreated and electropherogram the sample of electropherogram b) was pretreated in accordance with the present invention.
Figure 8B:
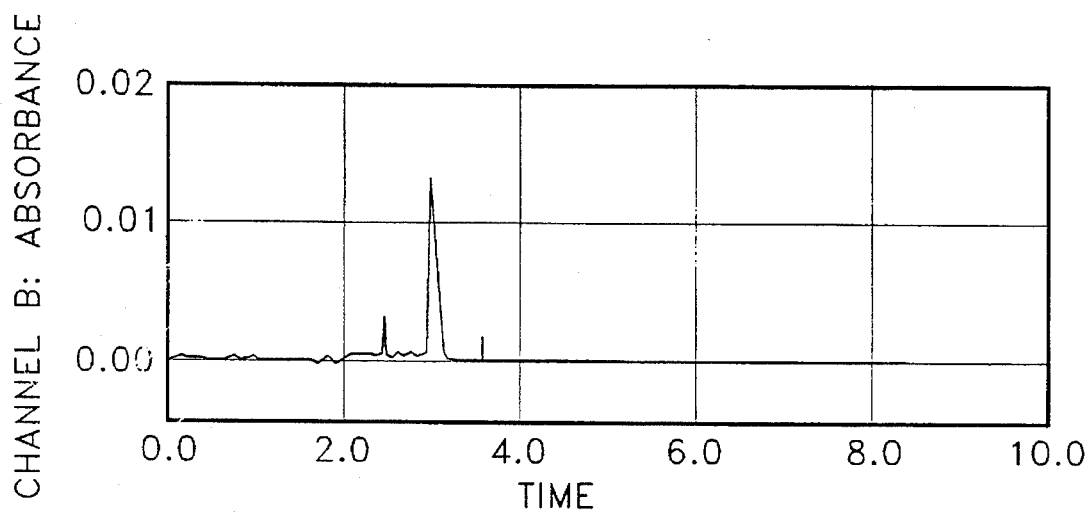

In order to demonstrate the efficacy and accuracy of the processes of the present invention utilizing a size exclusion gel having a molecular weight cut-off of about 6,000, a pathological urine sample was obtained from a proteinuria patient known to have an abnormally high amount of urine albumin. A first portion of the pathological sample was not pretreated with sized exclusion gel and analyzed by CZE as described in EXAMPLE 6. The resulting electropherogram is shown in FIG. 8 electropherogram a) where a number of components are shown, many of which appear to co-migrate.

A second portion of the pathological urine sample was treated with P-6 crosslinked polyacrylamide gel having a molecular weight cut-off of 6,000 in the same manner as described in EXAMPLE 1, sample b). The treated sample was then analyzed by CZE and electropherogram a) shown in FIG. 8 was obtained. This electropherogram clearly shows that albumin was excluded by the size exclusion gel and eluted as column eluent. Additionally, low molecular weight sample components are not evident in the electropherogram, evidencing their removal by the size exclusion gel.

EXAMPLE 9

In order to demonstrate the relative effectiveness of size exclusion gels having a molecular weight fractionation range of about 1,000 to 5,000 and a molecular weight cut-off of about 6,000 and size exclusion gels having a molecular weight cut-off of greater than 40,000 (and a molecular weight fractionation range of 2,500 to 40,000), a portion of the treated normal urine used in EXAMPLE 1 was spiked with trypsin inhibitor at a concentration of 1 mg/ml. Trypsin inhibitor has a molecular weight similar to that of Bence Jones proteins.

A CZE analysis was performed on the trypsin inhibitor spiked treated normal urine sample using the CZE analysis procedure described above. This provided a control electropherogram.

Next a portion of trypsin inhibitor spiked treated normal urine was treated again with P-30 crosslinked polyacrylamide gel as described in EXAMPLE 1. An electropherogram was obtained for the size exclusion gel treated sample using the CZE analysis procedure described above. Finally a portion of the trypsin inhibitor spiked treated normal urine was treated with crosslinked polyacrylamide gel as also described in EXAMPLE 1 except that the size exclusion gel was P-6 having a molecular weight cut-off of about 6,000.

Figure 9A:
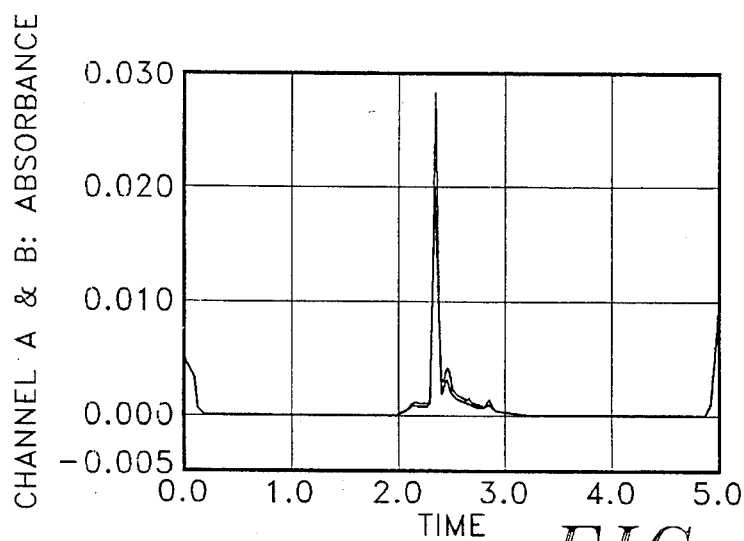
FIGS. 9a–c illustrate electropherograms obtained from urine samples which were pretreated in accordance with the present invention then spiked with trypsin inhibitor having a molecular weight of about 22,000. Electropherogram a) is an overlay of a spiked control sample which received no further treatment and a spiked sample pretreated with gel having a molecular weight fractionation range of about 2,500 - 40,000. Electropherogram b) is an overlay of a control sample which received no further treatment and a spiked sample pretreated with a gel having molecular weight fractionation range of 1,000 to 6,000. Electropherogram c) is an overlay of the spiked and subsequently pretreated samples of electropherogram a) and b).
Figure 9B:
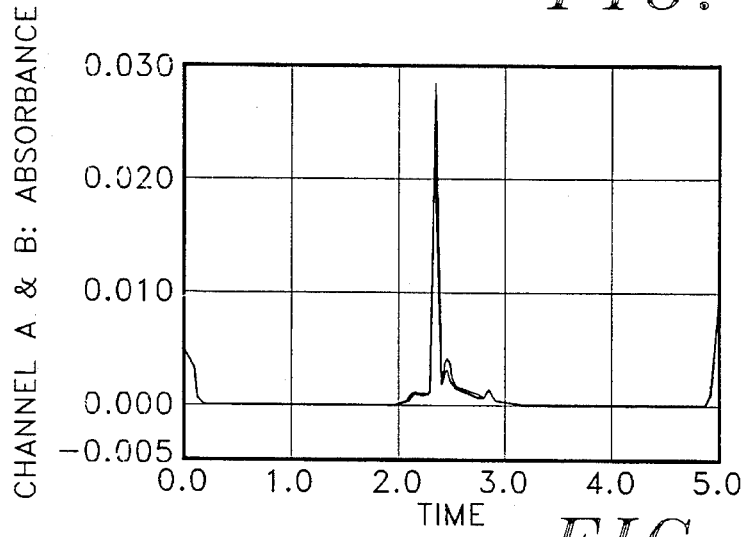
Figure 9C:
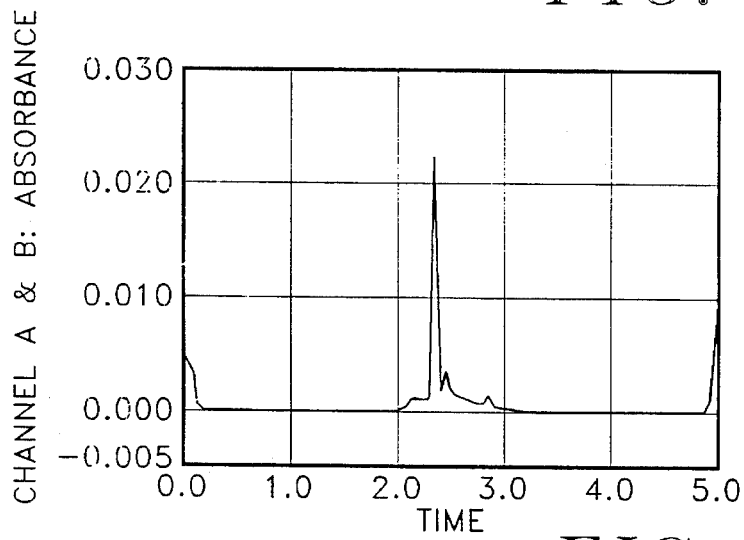

FIG. 9 illustrates electropherograms obtained using the trypsin inhibitor spiked urine. Electropherogram a) shows an overlay of the control electropherogram and the electropherogram obtained from the spiked sample treated with P-30 size exclusion gel. Electropherogram b) shows an overlay of the control electropherogram and the electropherogram obtained from the spiked sample treated with P-6 size exclusion gel. Finally, electropherogram c) shows an overlay of the electropherogram obtained from the spiked sample treated with P-6 and that obtained from the spiked sample treated with P-30. These clearly indicate the effectiveness of using both size exclusion gels in accordance with the present invention. The low molecular weight cut-off of the P-6 excluded all of the trypsin inhibitor and the molecular weight fractionation range of 2,500 to 30,000 easily fractionated the trypsin inhibitor so that it eluted from the column.

EXAMPLE 10

In order to compare the performance of a crosslinked polysaccharide (dextran) size exclusion gel and a crosslinked polyacrylamide gel, a pathological urine sample was obtained from a patient known to have Bence Jones proteins and treated as follows.

A portion of the pathological urine sample was treated with P-6 crosslinked polyacrylamide gel in the same manner as described in EXAMPLE 1 sample b). The treated sample was then analyzed by CZE using the same capillary and analytical conditions described above. A second portion of the pathological urine sample was treated with a crosslinked polysaccharide (dextran) size exclusion gel. The dextran gel utilized is available from Pharmacia under the trade name Sephadex-G-25 and has a molecular weight cut-off of as high as about 5,000. The second portion was treated with the gel in the same manner as the first portion and subsequently analyzed by CZE in the same manner.

Figure 10:
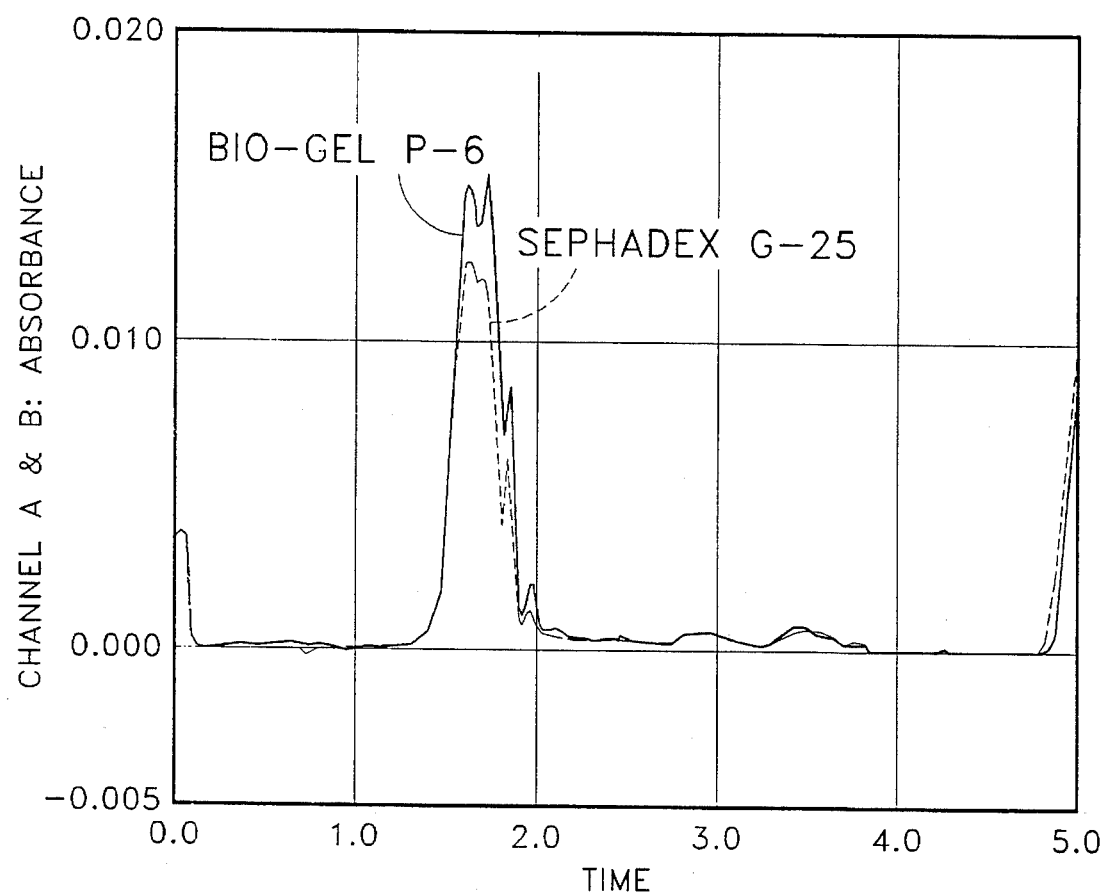
FIG. 10 illustrates electropherograms obtained from a myeloma patient urine samples pretreated with different gels with electropherogram a) obtained from a sample pretreated with a polyacrylamide gel and electropherogram b) obtained from a sample pretreated with a dextran gel.

FIG. 10 illustrates the electropherograms obtained from the two treated samples. Electropherogram a) was obtained from the sample pretreated with the polyacrylamide P-6 gel and electropherogram b) was obtained from the sample pretreated with the dextran gel. These electropherograms clearly demonstrate the two Bence Jones light chain peaks. It is also evident that size exclusion gels prepared from crosslinked dextran and size exclusion gels prepared from crosslinked polyacrylamide are effective and suitable in the practice of the present invention.

These results clearly illustrate that the processes of the present invention exclude low molecular weight components of urine samples and allow recovery of higher molecular weight proteins which can be indicative of a pathologically abnormal condition.

EXAMPLE 11

In order to demonstrate and compare the effectiveness of utilizing a polysaccharide size exclusion gel with a polyacrylamide gel to pretreat urine, a pathological urine sample containing an abnormal amount of albumin was obtained from a proteinuria patient. A portion of the proteinuria pathological urine sample was treated with P-6 crosslinked polyacrylamide gel in the same manner as described in EXAMPLE 1, for sample b). The treated sample was then analyzed by CZE utilizing analysis conditions described above.

Figure 11:
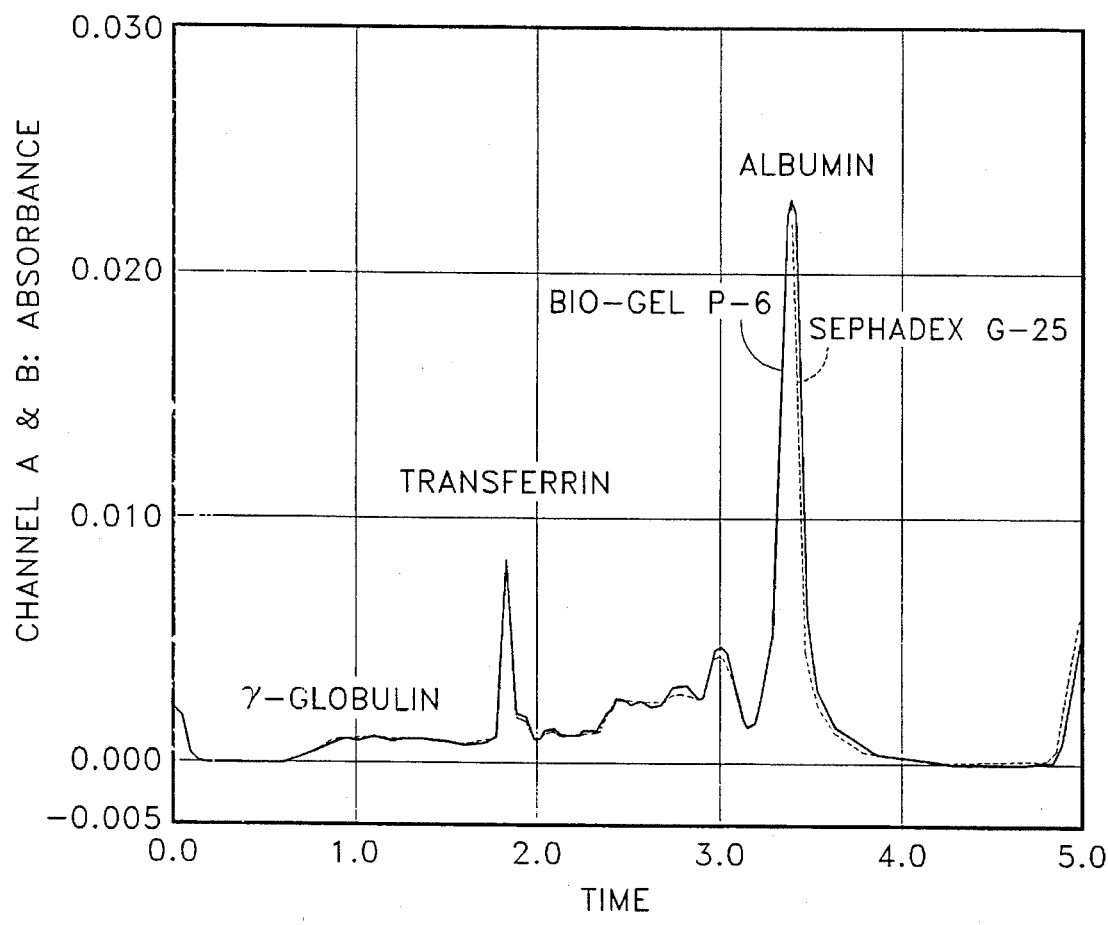
FIG. 11 illustrates electropherograms obtained from proteinuria patient urine samples pretreated with different gels with electropherogram a) obtained from a sample pretreated with a polyacrylamide gel and electropherogram b) obtained from a sample pretreated with a dextran gel.

A second portion of the pathological urine sample was treated in the same manner with the same crosslinked dextran size exclusion gel utilized in EXAMPLE 10, Sephadex G-25. This treated sample was analyzed subsequently using the same CZE procedures. FIG. 11 illustrates each of the electropherograms obtained from the CZE analysis of these pretreated samples. Electropherogram a), the solid line, was obtained from the sample pretreated with the P-6 size exclusion gel and electropherogram b), the dotted line, was obtained from the sample pretreated with Sephadex G-25 gel.

Both of these electropherograms clearly show the presence of serum proteins in urine associated with proteinuria patients. These proteins include gamma globulins, transferrin, and albumin. Moreover, these electropherograms indicate that interfering low molecular weight urine components are not present in the sample and the polyacrylamide gel and the polysaccharide gel are effective in allowing recovery of the proteins of interest.

Although the present invention has been described with regard to certain preferred methods, other embodiments, versions, and modification are contemplated as being within the scope of the present invention. For example, the use of size exclusion packed gels column described herein lend themselves to the automation of the invention described herein. More particularly, suitably sized size exclusion gel packed columns can be positioned in-line with a capillary electrophoresis system and samples can be pretreated, separated, and detected in an automatic fashion. This precludes the need for excess sample handling and can decrease the time required for each analysis. Accordingly, the spirit and scope of the present invention is limited only by the following claims.

What is claimed is:

1. A process for preparing an untreated clinical liquid sample for analysis, comprising the steps of:
   (a) selecting a size exclusion gel;
   (b) providing an untreated clinical liquid composition comprising low molecular weight components, and an unknown amount of a higher molecular weight analyte;
   (c) causing the untreated clinical liquid composition to contact the size exclusion gel; and (d) eluting the untreated clinical liquid composition from the size exclusion gel, to thereby obtain a size exclusion gel eluent, the eluent comprising substantially all of the higher molecular weight analyte and the eluent being substantially free of all of the low molecular weight components.

2. The process of claim 1 wherein providing said size exclusion gel is accomplished by packing said size exclusion gel in a column.

3. The process of claim 2 wherein causing said composition to contact said size exclusion gel is accomplished by passing said composition through said column, whereby the analyte is excluded or fractionated by said size exclusion gel.

4. The process of claim 1 wherein said size exclusion gel is prepared from a polymer selected from the group consisting of polyacrylamide gel and polysaccharide gel.

5. The process of claim 1 wherein said composition is mammalian urine.

6. The process of claim 5 wherein said analyte is selected from the group of proteins consisting of Bence Jones, albumin, transferrin, $\alpha_2$ macroglobin, immunoglobulin, haptoglobin and $\alpha_1$ antitrypsin.

7. The process of claim 1 wherein said size exclusion gel has a molecular weight fractionation range selected from the group consisting of 1,000–6,000 and 2,500 to 40,000.

8. The process of claim 1 wherein said size exclusion gel has a molecular weight cut-off of at least about 6,000.

9. A process for preparing an untreated urine sample for analysis of urine proteins having a molecular weight greater than 6,000, said process comprising the steps:

providing a column packed with size exclusion gel having a molecular weight cut-off of at least 6,000; and passing an untreated urine sample through said column, wherein said size exclusion gel excludes urine sample components having a molecular weight greater than 6,000.

10. The method of claim 9 wherein said size exclusion gel is prepared from polymers selected from the group consisting of polyacrylamide gels and polysaccharide gels.

11. The method of claim 9 wherein said urine sample components are selected from the group of proteins consisting of Bence Jones protein, albumin, transferrin, $\alpha_2$ macroglobin, haptoglobin, $\alpha_1$ antitrypsin and gamma globulin.

12. A process for pretreating, separating and determining an untreated clinical liquid sample comprising low molecular weighted components and an unknown amount of a higher molecular weight analyte said process comprising the steps:

providing size exclusion gel having a molecular weight fractionation range or molecular weight exclusion such that said exclusion gel is capable of fractionating or excluding said low molecular weight components;

causing said untreated clinical sample to contact said size exclusion gel to provide an eluent comprising said higher molecular weight analyte;

subjecting said eluent to electrophoresis; and detecting said higher molecular weight analyte.

13. The process of claim 12 wherein providing said size exclusion gel is accomplished by packing said size exclusion gel in a column.

14. The process of claim 13 wherein causing said clinical sample contact said size exclusion gel is accomplished by passing said clinical sample through said column to provide a column eluent comprising said analyte, whereby said analyte is excluded or fractionated by said size exclusion gel.

15. The process of claim 12 wherein said size exclusion gel is prepared from a polymer selected from the group consisting of polyacrylamide gel and polysaccharide gel.

16. The process of claim 12 wherein said clinical sample is mammalian urine.

17. The process of claim 12 wherein said analyte is selected from the group of proteins consisting of Bence Jones, albumin, transferrin, $\alpha_2$ macroglobin, immunoglobulin, haptoglobin, and $\alpha_1$ antitrypsin.

18. The process of claim 12 wherein said exclusion gel has a molecular weight cut-off of at least 6,000.

19. The process of claim 12 wherein subjecting said eluent to electrophoresis comprises the steps:

a) loading said eluent onto a electrophoresis buffer filled capillary; and b) subjecting said electrophoresis buffer filled capillary to an electric field.

20. A process for separating and determining at least one urine analyte in an untreated urine clinical sample, said analyte having a molecular weight greater than about 6,000, said process comprising the steps:

providing size exclusion gel having a molecular weight cut-off of at least about 6,000;

causing said untreated urine clinical sample to contact said size exclusion gel to provide an eluent comprising said analyte;

subjecting said eluent to capillary electrophoresis; and detecting said analyte.

* * * * *